MATERIALS AND METHODS FOR DELIVERY AND EXPRESSION OF HETEROLOGOUS DNA IN VERTEBRATE CELLS

United States Patent [19]
Moyer et al.
[11] Patent Number: 6,127,172
[45] Date of Patent: Oct. 3, 2000
[54] MATERIALS AND METHODS FOR DELIVERY AND EXPRESSION OF HETEROLOGOUS DNA IN VERTEBRATE CELLS
[75] Inventors: Richard W. Moyer; Yi Li, both of Gainesville, Fla.
[73] Assignee: University of Florida, Gainesville, Fla.
[21] Appl. No.: 09/086,651
[22] Filed: May 29, 1998
[51

The subject invention was made with government support under a research project supported by U.S. Department of Agriculture Grant No. 97-35302-4431 and National Institute of Health Grant No. P50-HL59412-01. The government has certain rights in this invention.

BACKGROUND OF THE INVENTION

Gene therapy is a powerful concept just now beginning to see applications designed to treat human diseases such as genetic disorders and cancer. The introduction of genes into an organism can be achieved in a variety of ways including virus based vectors. Viral gene therapy vectors can either be designed to deliver and express genes permanently (stable integration of a foreign gene into host chromosome) or transiently (for a finite period of time).

Current virus-based gene transfer vectors, are typically derived from animal viruses, such as retroviruses, herpesviruses, adenoviruses, or adeno-associated viruses. Generally, these viruses are engineered to remove one or more genes of the virus. These genes may be removed because they are involved in viral replication and/or to provide the capacity for insertion and packaging of foreign genes. Each of these known vectors has some unique advantages as well as disadvantages. One primary disadvantage is an inability to readily package and deliver large DNA inserts that are greater than 10 kb in size.

To illustrate the problem of capacity of most gene therapy vectors, one need only consider adeno-associated virus (AAV), one of the most promising of the gene therapy vectors. Adeno-associated virus (AAV) is a parvovirus which consists of a 4.7 kb single stranded DNA genome (Nienhuis et al., 1983). The viral genome consists of the family of rep genes responsible for regulatory function and DNA replication and the cap genes that encode the capsid proteins. The AAV coding region is flanked by 145 nucleotide inverted terminal repeat (ITR) sequences which are the minimum cis-acting elements essential for replication and encapsidation of the genome. In the absence of a helper virus such as adenovirus, AAV causes a latent infection characterized by the integration of viral DNA into the cellular genome. The major advantages of recombinant AAV (rAAV) vectors include a lack of pathogenicity in humans (Berns and Bohenzky, 1987), the ability of wild-type AAV to integrate stably into the long arm of chromosome 19 (Kotin et al., 1992), the potential ability to infect nondividing cells (Kaplitt et al., 1994), and broad range of infectivity. However, the packaging capacity of AAV limits the size of the inserted heterologous DNA to about 4.7 kb.

Gene therapy vector systems are also needed that combine a large carrying capacity with high transduction efficiency in vivo. We describe here a new gene delivery system which has a large capacity for insertion of foreign genes and which integrates stably into host chromosome.

Entomoxpoxvirus (EPVs) productively infect and kill only insects (Granados, 1981) and can be isolated from *Amsacta moorei* (AmEPV), the red hairy caterpillar. Entomopox viruses and vectors have been described (See, for example, U.S. Pat. Nos. 5,721,352 and 5,753,258, the disclosure of which is incorporated herein by reference). Like other EPVs, AmEPV cannot productively infect vertebrate cells. Indeed, following addition of AmEPV to vertebrate (mouse L-929) cells at multiplicities up to 10 particles/cell, no chances in cellular morphology (as judged by phase contrast microscopy) are detected (Langridge, 1983).

AmEPV infects vertebrate cells in a non-cytocidal manner and the infection is abortive. Like all poxviruses, the virus is cytoplasmic and does not normally enter the nucleus. A consequence of this unusual biology, is that all poxvirus mediated gene expression takes place in the cytoplasm in the infected cell. AmEPV promoters and those of the eucaryotic cell are completely different and cellular promoters are not recognized by the AmEPV transcription machinery nor are AmEPV viral promoters recognized by RNA polymerase II of the host cell.

BRIEF SUMMARY OF THE INVENTION

The subject invention concerns a novel viral vector system for gene therapy based on an insect poxvirus designed to deliver genes for integration and stable, permanent expression in vertebrate cells. In an exemplified embodiment, a recombinant AmEPV vector was constructed that contains heterologous genes under the control of promoters that the drive expression of the heterologous genes in vertebrate cells. The gfp gene and the gene encoding G418 resistance were used in an exemplified construct. The recombinant AmEPV was used to infect vertebrate cells and following infection the cells were transferred to media containing G418. Cells expressing both GFP and G418 resistance were obtained. Thus, the vectors of the subject invention can be used to deliver large DNA segments for the engineering of vertebrate cells.

The subject invention also concerns cells that have been infected with or transformed with a recombinant vector of the present invention. The subject invention also concerns methods for providing gene therapy for conditions or disorders of an animal requiring therapy, such as genetic deficiency disorders.

DETAILED DISCLOSURE OF THE INVENTION

Figure 1:
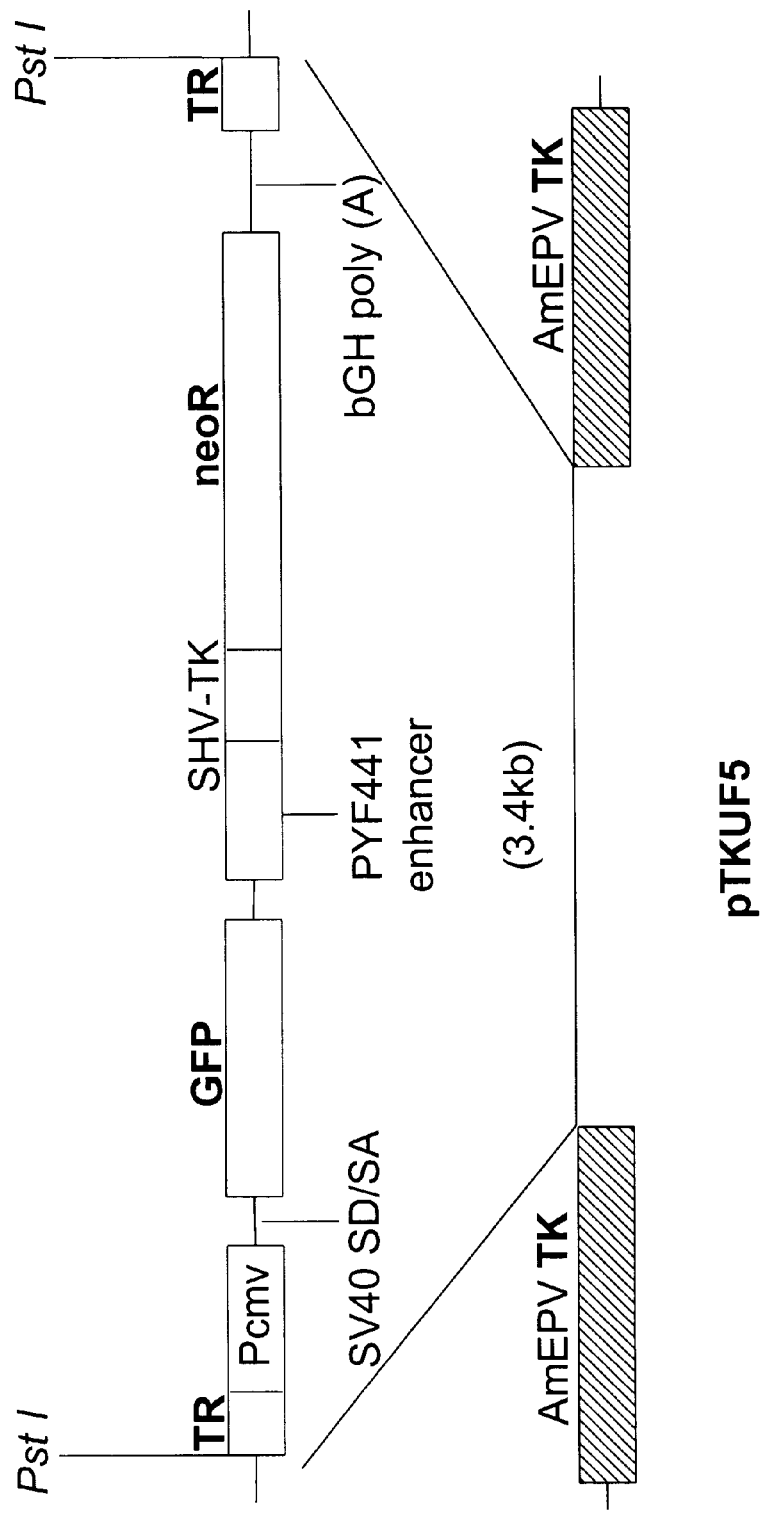
FIG. 1 shows a physical map of an exemplified recombinant vector of the subject invention (pAmEPV TKUF5) in which a portion of the plasmid pTKUF5 has been cloned within the AmEPV TK gene flanking regions. TR is the AAV terminal repeat, pA is a polyadenylation site, SD/SA is the SV40 late splice donor, splice acceptor sequence. GFP is under the control of a CMV promoter, Neo is under the control of a herpes TK gene promoter.

The subject invention concerns novel recombinant vectors and methods for delivery and expression of heterologous polynucleotides in vertebrate cells. The recombinant vectors of the subject invention provide for stable integration and expression of heterologous DNA in the host cell. Advantageously, the vectors of the invention are adapted for accepting large heterologous polynucleotide inserts which can be delivered and stably expressed in an infected or transformed cell. The subject invention can be used to provide gene therapy for conditions or disorders of vertebrate animals, such as a mammal or human, that is in need of such therapy.

One aspect of the subject invention concerns a recombinant EPV vector which can optionally include heterologous DNA which can be expressed in a cell infected or transformed with the subject vector. Preferably, the EPV vector is derived from AmEPV. The recombinant EPV vectors of the present invention can optionally include inverted terminal repeat (ITR) sequences of a virus, such as, for example, adeno-associated virus, that flank the heterologous DNA insertion site on the vector. Thus, when the heterologous DNA is cloned into the recombinant EPV vector, the heterologous DNA is flanked upstream and downstream by the ITR sequences.

In an exemplified embodiment, the subject vectors comprise heterologous DNA inserted within the vector. The heterologous DNA contained within the recombinant vectors of the invention can include polynucleotide sequences which encode a biologically functional protein. Preferably, the polynucleotides encode proteins which can provide therapeutic replacement or supplement in animals afflicted with disorders which result in the animal expressing abnormal or deficient levels of the protein that are required for normal biological function. Proteins encoded by the heterologous DNA can include, but are not limited to interleukins, cytokines, growth factors, interferons, enzymes, and structural proteins. Protein encoded by the heterologous DNA can also include proteins that provide a selectable marker for expression, such as antibiotic resistance in eukayotes.

In a preferred embodiment, heterologous DNA within the subject vectors is operably linked with and under the control of regulatory sequences, such as promoters. The recombinant vectors of the invention preferably comprises a constitutive or regulatable promoter capable of promoting sufficient levels of expression of the heterologous DNA contained in the viral vector in a vertebrate cell. Promoters useful with the subject vectors include, for example, the cytomegalovirus (CMV) promoters and the herpes TK gene promoter. The vectors can also include other regulatory elements such as introns inserted into the polynucleotide sequence of the vector.

The subject invention also concerns cells containing recombinant vectors of the present invention. The cells can be, for example, vertebrate cells such as mammalian cells. Preferably, the cells are human cells. Cell lines infected or transformed with the recombinant vectors of the present invention are also within the scope of the invention.

The recombinant vectors of the present invention can be introduced into suitable cells or cell lines by methods known in the art. If the recombinant vectors are packaged in viral particles then cells or cell lines can be infected with the virus containing the recombinant vector. Methods contemplated for introducing recombinant vector into cells or cell lines also include transfection, transduction and injection. For example, vectors can be introduced into cells using liposomes containing the subject recombinant vectors. Recombinant viral particles and vectors of the present invention can be introduced into cells by in vitro or in vivo means.

Infection of vertebrate cells is non-permissive, and that early but not late AmEPV gene expression occurs (Li et al., 1997). Specifically, if a reporter gene, such as lacZ is driven by a late poxvirus promoter, either the AmEPV spheroidin or cowpox virus ATI (A-type Inclusion) promoter, no expression of galactosidase is observed. If, however, the lacZ is driven instead by either of two early EPV promoters (the *Melolontha melolontha* EPV fusolin gene promoter (Gauthier et al., 1995) or the 42 kDa early AMEPV protein (Li et al., 1997)), high levels of galactosidase in the recombinant AmEPV infected vertebrate cells are observed. These results provide clear evidence of AmEPV entry into vertebrate cells followed by early, but not late, viral gene expression.

It has also been found that vertebrate cells survive infection by AmEPV. If CV-1 cells are infected with an AmEPV recombinant which contains the green fluorescent protein (GFP) gene regulated by the 42 kDa AmEPV early promoter (also called the esp promoter), single, fluorescent cells are initially observed which then proceed to grow and divide, ultimately forming small clusters of fluorescent cells. Therefore, AmEPV enters vertebrate cells, to produce a non-permissive, abortive infection, early viral genes are expressed and infected cells appear to survive and continue to divide. These properties plus a very large capacity of the virus for foreign genes make AmEPV an excellent vector for delivery of genes for expression in a transient fashion.

Materials and Methods

Cells and virus.

AMEPV (Hall and Moyer, 1991) was replicated in IPLB-LD-652 cells (Goodwin et al., 1990) which were maintained at 28° C. in a 1:1 mixed medium (TE medium) of TC-100 media (Gibco, Gaithersburg, Md.) and EX-CELL 401 media (JRH Biosciences, Lenexa, Kans.), supplemented with 10% fetal bovine serum. A TK negative cell line designated C11.3 was selected by a process of adaption of TK(+)LD652 cell to increasing levels, 10 µg/ml every 5 weeks, of 5-bromo-2'-deoxyuridine (BudR) over one year up to 100 µg/ml BudR and maintained in TE medium containing BudR (100 µg/ml). 293 cells were grown in DMEM medium supplemented with 5% fetal bovine serum.

Plasmid construction and preparation of AmEPV recombinant.

pTR-UF5 (see FIG. 1, provided by the Vector Core, Gene Therapy Center, University of Florida) contains GFP and NeoR genes under control CMV promoter and herpes virus TK promoter respectively and flanked by ITR sequences of AAV. The Pst I fragment which contains GFP and NeoR markers was inserted into Pst I site of pTKDU (Li et al., 1998) to produce pTKUF5. AMEPV recombinant with an insert in the TK gene was obtained as described previously (Li et al., 1998).

Following are examples which illustrate procedures for practicing the invention. These examples should not be construed as limiting. All percentages are by weight and all solvent mixture proportions are by volume unless otherwise noted.

EXAMPLE I

Gene Expression in Cells Infected with Recombinant AmEPV 293 cells (1×10$^6$) were placed in 6-well plate and infected with recombinant AmEPVpTKUF5 or AmEPVpTKespgfp (Li et al., 1997) viruses at a multiplicity of five (5) virus particles/cell. As controls, cells were separately transfected with either the plasmid pTR-UF5 or pTKUF5 at a 5 µg/well plasmid DNA. Two days later, virus infected or plasmid transfected cells were transferred into 60 mm dishes, after 24 hr, neomycin resistant colonies were selected by adding G418 at the final concentration of 200 µg/ml. G418 containing medium was changed every 3–4 days.

For cells infected with recombinant AmEPV pTKespgfp, no neomycin resistant colony was observed, an expected result since this virus does not have NeoR gene. However, cells infected with recombinant AmEPV pTKUF5 or transfected with plasmids pTR-UF5, G418 resistant colonies were observed. All colonies from cells transfected with either of the two plasmids were both G418 resistant and GFP positive. However, colonies from cells infected with recombinant pTKUF5 were initially only G418 resistant, and not GFP positive. G418 resistant colonies derived from the AmEPV recombinant also grew more slowly than those produced following plasmid transfection. Most likely, the explanation for these results is that GFP and NeoR gene copy number in AmEPV derived colonies is less than those transfected with plasmids. This explanation is likely to be true as we were able to show that the AmEPV derived colonies gradually become more and more resistant to G418 and soon, some GFP positive clusters of cells were observed which become more numerous and brighter. After several changes of medium, ultimately, all cells in the well were GFP positive.

It should be understood that the examples and embodiments described herein are for illustrative purposes only and that various modifications or changes in light thereof will be suggested to persons skilled in the art and are to be included within the spirit and purview of this application and the scope of the appended claims.

References

U.S. Patents
U.S. Pat. No. 5,721,352
U.S. Pat. No. 5,753,258

Other References

Berns, K. I. and R. A. Bohenzky (1987) "Adeno-associated viruses: an update. *Adv. Virus Res.* 32: 243–306.

Gauthier, L., F. Coussrans, J. C. Veyrunes, M. Bergoin (1995) "The *Melolontha melolontha* entomopoxvirus (MmEPV) fusolin is related to the fusolins of lepidoptera EPVs and to the 37 K baculovirus glycoprotein" *Virology* 208:427–436.

Granados, R. R. (1981) "Entomopoxvirus infections in insects, In Pathogenesis of invertebrate Microbial Disease, p. 102–126, Davidson, E. W. (ed.) New Jersey, Allanheld Totowa.

Kaplitt et al. (1994) "Long term gene expression and phenotypic correction using adeno-associated virus vectors in the mammalian brain" *Nat. Genet* 8:148–154.

Kotin, R. M., R. M. Linden, K. I. Berns (1992) "Characterization of a preferred site on human chromosome 10q for integration of adeno-associated virus DNA by nonhomologous recombination" *EMBO J* 11:5071–5078.

Langridge, W. H. (1983) "Detection of *Amsacta moorei* entomopoxvirus and vaccinia virus proteins in cell cultures restrictive for poxvirus multiplication" *J. Invertebr. Pathol.* 42:77–82.

Li, Y., R. L. Hall, R. W. Moyer (1997) "Transient, nonlethal expression of genes in vertebrate cells by recombinant entomopoxviruses" *J. Virol.* 71:9557–9562.

Li, Y., R. L. Hall, S. L. Yuan, R. W. Moyer (1998) "High level expression of *Amsacta moorei* entomopoxvirus Spheroidin depends on sequences within the gene" *J. Gen. Virol.* 79:613–622.

Nienhuis, A. W., C. E. Walsh, J. M. Liu (1993) "Viruses as therapeutic gene transfer vectors" In: N. S. Young (ed.) Viruses and bone marrow, Marcel Decker, New York, p353–414.

What is claimed is:

1. A method for transforming a vertebrate cell to confer on said cell the ability to express a desired protein, said method comprising introducing into said cell in vitro an effective amount of a recombinant entomopox virus vector, wherein said vector comprises a polynucleotide encoding said protein operably linked to an early promoter sequence wherein said promoter drives the expression of said polynucleotide in said vertebrate cell.

2. The method according to claim 1, wherein said vertebrate cell is a mammalian cell.

3. The method according to claim 2, wherein said mammalian cell is a human cell.

4. The method according to claim 1, wherein said vector comprises inverted terminal repeat sequences flanking said polynucleotide encoding said protein.

5. The method according to claim 4, wherein said inverted terminal repeat sequences are derived from adeno-associated virus.

6. The method according to claim 1, wherein said early promoter sequence is selected from the group consisting of CMV promoter sequences and herpes TK promoter sequences.

7. The method according claim 1, wherein said protein encoded by said polynucleotide is selected from the group consisting of interleukins, cytokines, growth factors, interferons, enzymes and structural proteins.

8. The method according to claim 1, wherein said vector is introduced into said vertebrate cells by infection in a viral particle.

9. The method according to claim 1, wherein said vector is introduced into said vertebrate cells by means selected from the group consisting of transfection and transduction injection.

10. The method according to claim 1, wherein said polynucleotide encoding said protein is greater than about 10 kb in size.

11. The method according to claim 1, wherein said polynucleotide further encodes a selectable marker protein operably linked to a second early promoter sequence.

12. A recombinant entomopox virus vector comprising a polynucleotide encoding a protein operably linked to a heterologous early promoter sequence, wherein said heterologous early promoter sequence drives the expression of said polynucleotide in vertebrate cells.

13. A recombinant entomopox virus vector comprising a polynucleotide encoding a protein operably linked to a heterologous early promoter sequence, wherein said heterologous early promoter sequence drives the expression of said polynucleotide in vertebrate cells, and wherein said polynucleotide encoding said protein is greater than about 10 kb in size.

14. The vector according to claim 13, wherein said entomopox virus is *Amsacta moorei.*

15. The vector according to claim 13, wherein said vector comprises inverted terminal repeat sequences flanking said polynucleotide encoding said protein.

16. The vector according to claim 15, wherein said inverted terminal repeat sequences are derived from adeno-associated virus.

17. The vector according to claim 15, wherein said early promoter sequence is selected from the group consisting of CMV promoter and herpes TK promoter sequences.

18. The vector according to claim 13, wherein said protein encoded by said polynucleotide is selected from the group consisting of interleukins, cyokines, growth factors, interferons, enzymes and structural proteins.

19. The vector according to claim 13, wherein said polynucleotide further encodes a selectable marker protein operably linked to a second early promoter sequence.

20. A viral particle comprising the vector of claim 13.

21. An isolated vertebrate cell comprising a recombinant entomopox virus vector comprising a polynucleotide encoding a protein operably linked to an early promoter sequence, wherein said early promoter sequence drives the expression of said polynucleotide in said isolated vertebrate cell.

* * * * *

UNITED STATES PATENT AND TRADEMARK OFFICE
CERTIFICATE OF CORRECTION

PATENT NO. : 6,127,172

DATED : October 3, 2000

INVENTOR(S) : Richard W. Moyer, Yi Li

It is certified that error appears in the above-identified patent and that said Letters Patent is hereby corrected as shown below:

Column 2, line 2: "chances" should read --changes--.

Column 3, line 23: "eukayotes." should read --eukaryotes.--.

Column 6, line 49: "claim 15" should read --claim 13--.

Signed and Sealed this

Eighth Day of May, 2001

*Attest:*

NICHOLAS P. GODICI

*Attesting Officer*    *Acting Director of the United States Patent and Trademark Office*